(12) United States Patent
Prasad et al.

(10) Patent No.: US 7,628,984 B2
(45) Date of Patent: *Dec. 8, 2009

(54) MICRONUTRIENT FORMULATIONS FOR PULMONARY AND HEART HEALTH

(75) Inventors: Kedar N. Prasad, San Rafael, CA (US); Gerald M. Haase, Greenwood Village, CO (US); William C. Cole, Novato, CA (US)

(73) Assignee: Premier Micronutrient Corporation, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/157,077

(22) Filed: Jun. 6, 2008

(65) Prior Publication Data

US 2008/0241119 A1    Oct. 2, 2008

Related U.S. Application Data

(63) Continuation-in-part of application No. 11/357,246, filed on Feb. 17, 2006, now Pat. No. 7,399,755.

(60) Provisional application No. 60/653,700, filed on Feb. 17, 2005.

(51) Int. Cl.
| A61K 31/122 | (2006.01) |
| A61P 11/00  | (2006.01) |
| A61P 9/00   | (2006.01) |

(52) U.S. Cl. .................................................... 424/94.1
(58) Field of Classification Search ................... 514/52, 514/188, 167, 251, 458, 474, 494, 574, 725
See application file for complete search history.

(56) References Cited

U.S. PATENT DOCUMENTS

| 5,292,538 | A  | * | 3/1994  | Paul et al. ................. 426/74 |
| 5,561,160 | A  | * | 10/1996 | Walaszek et al. ........... 514/574 |
| 5,626,883 | A  | * | 5/1997  | Paul ........................... 424/605 |
| 5,661,123 | A  | * | 8/1997  | Stalker et al. ................ 514/2 |
| 5,895,652 | A  | * | 4/1999  | Giampapa ............... 424/195.17 |
| 5,976,568 | A  | * | 11/1999 | Riley .......................... 424/451 |
| 6,139,872 | A  | * | 10/2000 | Walsh ......................... 424/464 |
| 6,245,360 | B1 | * | 6/2001  | Markowitz ................. 424/641 |
| 6,291,533 | B1 | * | 9/2001  | Fleischner ................. 514/682 |
| 6,503,529 | B1 | * | 1/2003  | Fleischner ................. 424/439 |
| 6,646,013 | B1 | * | 11/2003 | Barker et al. ............... 514/731 |
| 6,660,293 | B2 | * | 12/2003 | Giordano et al. ........... 424/439 |
| 6,686,340 | B2 | * | 2/2004  | Rath ........................... 514/52 |
| 6,693,129 | B2 | * | 2/2004  | Rath ........................... 514/474 |
| 6,733,797 | B1 | * | 5/2004  | Summers ................... 424/728 |
| 6,845,777 | B2 | * | 1/2005  | Pera ........................... 131/270 |
| 6,849,613 | B2 | * | 2/2005  | Prasad et al. ................ 514/52 |
| 2001/0031744 | A1 | * | 10/2001 | Kosbab ....................... 514/54 |
| 2003/0190381 | A1 | * | 10/2003 | Bland et al. ................. 424/757 |
| 2005/0037065 | A1 | * | 2/2005  | Kirschner et al. ........... 424/456 |
| 2006/0105033 | A1 | * | 5/2006  | Bendich ..................... 424/451 |

* cited by examiner

Primary Examiner—Brian-Yong S Kwon
(74) Attorney, Agent, or Firm—Dan M. DeLa Rosa

(57) ABSTRACT

A heart and pulmonry health micronutrient formulation is provided and the formulation comprises dietary antioxidants and endogenous antioxidants, and the formulation comprising dietary micronutrients and endogenous antioxidants, the dietary antioxidants are selected from a group consisting essentially of Vitamin A (Palmitate), Vitamin E, Vitamin C, Vitamin $D_3$ (Cholecalciferol), B Vitamins, Biotin, Pantothenic Acid (as D-Calcium Pantothenate), Calcium Citrate, Magnesium Citrate, Zinc Glycinate, Selenium (Seleno-L-Methionine), Chromium (as Chromium Picolinate), Mixed Carotenoids and mixtures thereof, and the endogenous antioxidants are selected from a group consisting essentially of N-Acetyl Cysteine (NAC), Coenzyme $Q_{10}$, R-alpha Lipoic Acid, Omega-3 fatty Acid, and L-Carnitine and mixtures thereof.

6 Claims, No Drawings

MICRONUTRIENT FORMULATIONS FOR PULMONARY AND HEART HEALTH

RELATED APPLICATION

This application is a continuation-in-part of U.S. application Ser. No. 11/357,246, entitled "Formulations Comprising Multiple Dietary And Endogenously Made Antioxidants And B-Vitamins And Use Of The Same" which was filed on Feb. 17, 2006, now U.S. Pat. No. 7,399,755, and has now been granted a Notice of Allowance, which claims the priority of Provisional Application No. 60/653,700 filed Feb. 17, 2005.

BACKGROUND OF THE INVENTION

1. Field of the Invention

The invention is directed to formulations comprised of multiple dietary and endogenous antioxidants and B-vitamins for the prevention and treatment coronary artery diseases, and pulmonary and heart diseases and disorders.

2. Description of the Related Art

Coronary artery disease (CAD) remains the number one cause of death in the U.S.A. About 1.5 million new cases are detected annually, and approximately 1 million people die of this disease every year. The current estimate is that about 62 million Americans have one or more types of cardiovascular disease, and about 14 million per year suffer from heart attack or angina. The direct and indirect cost in the U.S.A. of this disease is estimated to be about 329 billion dollars annually.

Various organizations and health professional have proposed primary prevention strategies that involve changes in the diet and lifestyle. Although these recommendations appear rational, they have not had any significant impact in reducing the risk of heart disease. This may be due to the fact that most people do not follow lifestyle changes and diet modifications, and those who do follow them do not start until atherosclerosis is well established. At present, statin with or without niacin is recommended to patients with high LDL-cholesterol and low HDL-cholesterol, and aspirin for the primary prevention as well as treatment of CAD. However, some patients at high cholesterol-lowering drug doses may exhibit muscle pain and liver toxicity, and a significant number of these patients develop varying degrees of aspirin resistance. Therefore, the current strategy for the prevention and treatment of CAD needs improvement.

Since increased oxidative stress and homocysteine level are considered major risk factors in the etiology of CAD, it appears rational to suggest that daily supplementation with multiple dietary and endogenously made antioxidants together with B-vitamins may enhance the efficacy of the current strategies for the prevention and treatment of CAD. Although the U.S. Prevention Service Task Force recommends vitamin supplements to reduce the risk of cancer and CAD, the role of antioxidants alone or in combination with standard therapy in the prevention or treatment of CAD has become a controversial and confusing issue for the public as well as professionals. This is due to the fact that interventional trials with dietary antioxidants, mostly with vitamin E alone or in combination with cholesterol-lowering drugs, have produced inconsistent results, varying from a beneficial effect to no effect to a harmful effect.

A few excellent reviews have summarized the published data on these issues, but did not identify possible reasons for inconsistent results of interventional trials with antioxidants, and did not propose any specific recommendations for the prevention or as adjunct to standard therapy the treatment of CAD. Based on the current inconsistent results of intervention studies, it is inappropriate to promote the notion that antioxidants have no value in the prevention or treatment of CAD or that they may have adverse effects in CAD patients taking statins and/or niacin.

SUMMARY OF THE INVENTION

In one embodiment, the present invention provides for micronutrient formulation for treatment of heart and pulmonary diseases and disorders, and the formulation consisting essentially of:
Vitamin A (Palmitate),
Vitamin E,
Vitamin C,
Vitamin $D_3$ (Cholecalciferol),
B Vitamins
Biotin
Pantothenic Acid (as D-Calcium Pantothenate)
Calcium Citrate
Magnesium Citrate
Zinc Glycinate
Selenium (Seleno-L-Methionine)
Chromium (as Chromium Picolinate)
N-Acetyl Cysteine (NAC)
Coenzyme $Q_{10}$
Alpha Lipoic Acid
Omega-3 Fatty Acid
L-Carnitine and
Natural Mixed Carotenoids.

In another embodiment, Vitamin E is selected from a group consisting essentially of alpha tocopherol and derivative esters of alpha tocopherol, and mixtures thereof. In yet another embodiment, the derivative esters of alpha tocopherol are selected from a group consisting essentially of alpha tocopheryl acetate, alpha tocopheryl palmitate, alpha tocopheryl succinate, alpha tocopheryl nicotinate and mixtures thereof.

In still another embodiment, B Vitamins are selected from a group consisting essentially of Vitamin $B_1$ (Thiamine Mononitrate), Vitamin $B_2$ (Riboflavin), Vitamin $B_3$ (Niacinamide Ascorbate), Vitamin $B_6$ (Pyridoxine Hydrochloride), Folic Acid, Vitamin $B_{12}$ (Cyanocobalamln) and mixtures thereof.

In still yet another embodiment, the mixed carotenoids are selected from a group consisting essentially of natural sources of algae, alpha carotene, beta carotene, gamma carotene, lutein, lycopene, xynthines, beta-cryptoxanthin, zeaxanthin, astaxanthin, phytoene, canthaxanthin, fucoxanthin and mixtures thereof.

In a further embodiment, Vitamin E is selected from a group consisting essentially of Buffered Vitamin C (calcium ascorbate), Vitamin C and mixtures thereof.

In still a further embodiment, the formulation is consumed by the user at least twice per day. In yet a further embodiment, the formulation is consumed by the user prior to diagnosis of pulmonary and heart related diseases. In still yet a further embodiment, the formulation is consumed by the user for long term maintenance after diagnosis of pulmonary and heart related diseases. In another further embodiment, the long term maintenance is from about at least one week to about life long.

In yet another further embodiment, the present invention relates to a formulation for pulmonary and heart related diseases, and the formulation comprising dietary micronutrients and endogenous antioxidants, the dietary antioxidants are selected from a group consisting essentially of Vitamin A (Palmitate), Vitamin E, Vitamin C, Vitamin $D_3$ (Cholecalciferol), B Vitamins, Biotin, Pantothenic Acid (as D-Calcium Pantothenate), Calcium Citrate, Magnesium Citrate, Zinc Glycinate, Selenium (Seleno-L-Methionine), Chromium (as Chromium Picolinate), Mixed Carotenoids and mixtures thereof, and the endogenous antioxidants are selected from a group consisting essentially of N-Acetyl Cysteine (NAC), Coenzyme $Q_{10}$, R-alpha Lipoic Acid, Omega-3 fatty Acid, and L-Carnitine and mixtures thereof, wherein said formulation is designed for pulmonary and heart health.

In still another further embodiment, Vitamin E is selected from a group consisting essentially of alpha tocopherol and derivative esters of alpha tocopherol, and mixtures thereof. In still yet another further embodiment, the derivative esters of alpha tocopherol are selected from a group consisting essentially of alpha tocopheryl acetate, alpha tocopheryl palmitate, alpha tocopheryl succinate, alpha tocopheryl nicotinate and mixtures thereof.

In another embodiment, B Vitamins are selected from a group consisting essentially of Vitamin $B_1$ (Thiamine Mononitrate), Vitamin $B_2$ (Riboflavin), Vitamin $B_3$ (Niacinamide Ascorbate), Vitamin $B_6$ (Pyridoxine Hydrochloride), Folic Acid, Vitamin $B_{12}$ (Cyanocobalamln) and mixtures thereof.

In still another embodiment, the mixed carotenoids are selected from a group consisting essentially of natural sources of algae, alpha carotene, beta carotene, gamma carotene, lutein, lycopene, xynthines, beta-cryptoxanthin, zeaxanthin, astaxanthin, phytoene, canthaxanthin, fucoxanthin and mixtures thereof.

In yet another embodiment, Vitamin E is selected from a group consisting essentially of Buffered Vitamin C (calcium ascorbate), Vitamin C and mixtures thereof.

In a further embodiment, the formulation consists essentially of:
Vitamin A (Palmitate) from about 3,000 to about 5,000 I.U.,
Vitamin E from about 50 to about 400 I.U.
Vitamin C from about 100 to about 4,000 I.U.,
Vitamin $D_3$ (Cholecalciferol) from about to about 400 to about 600 I.U.,
B Vitamins from about 2 to about 1,200 mg,
Biotin from about 100 to about 500 mcg,
Pantothenic Acid (as D-Calcium Pantothenate) from about 5 to about 30 mg,
Calcium Citrate from about 100 to about 500 mg,
Magnesium Citrate from about 100 to about 250 mg,
Zinc Glycinate from about 10 to about 30 mg,
Selenium (Seleno-L-Methionine) from about 50 to about 200 mcg,
Chromium (as Chromium Picolinate) to about 50 to about 200 mcg,
N-Acetyl Cysteine (NAC) from about 100 to about 500 mg,
Coenzyme $Q_{10}$ from about 10 to about 250 mg,
Alpha Lipoic Acid from about 15 to about 100 mg,
Omega-3 Fatty Acid from about 1,000 to about 4,000 mg,
L-Carnitine from about 50 to about 500 mg, and
Natural Mixed Carotenoids from about 10 to about 20 mg.

In another further embodiment, the present invention relates to a hearing health formulation comprising first and second compositions, and the first composition consisting essentially of:
Vitamin A (Palmitate) from about 3,000 to about 5000 IU
Vitamin E from about 50 to about 400 IU
Buffered Vitamin C (Calcium Ascorbate) from about 100 to about 4,000 mg
Vitamin C from about 100 to about 4,000 mg
Vitamin $D_3$ (Cholecalciferol) from about 400 to about 600 IU
Vitamin $B_1$ (Thiamine Mononitrate) from about to 2 about 10 mg
Vitamin $B_2$ (Riboflavin) from about 2 to about 20 mg
Vitamin $B_3$ (Niacinamide Ascorbate) from about 15 to about 200 mg
Vitamin $B_6$ (Pyridoxine Hydrochloride) from about 2 to about 10 mg
Folic Acid from about 400 to about 1500 mcg
Vitamin $B_{12}$ (Cyanocobalamln) from about 5 to about 20 mcg
Biotin from about 100 to about 500 mcg
Pantothenic Acid (as D-Calcium Pantothenate) from about 5 to about 30 mg
Calcium Citrate from about 100 to about 500 mg
Magnesium Citrate from about 100 to about 250 mg
Zinc Glycinate from about 10 to about 30 mg
Selenium (Seleno-L-Methionine) from about 50 to about 200 mcg
Chromium (as Chromium Picolinate) from about 50 to about 200 mcg, said the second composition consisting essentially of:
N-Acetyl Cysteine (NAC) from about 100 to about 500 mg
Coenzyme $Q_{10}$ from about 10 to about 250 mg
Alpha Lipoic Acid from about 15 to about 100 mg
Omega-3 Fatty Acid from about 1,000 to about 4,000 mg
Natural Mixed Carotenoids from about 10 to about 20 mg and
L-Carnitine from about 50 to about 500 mg and wherein the formulation is designed to treat heart and pulmonary diseases and disorders.

In a further embodiment, Vitamin E is selected from a group consisting essentially of d-alpha Tocopheryl Succinate from about 50 to about 400 IU, d-alpha Tocopheryl Acetate from about 50 to about 400 IU and mixtures thereof, said mixed carotenoids are selected from a group consisting essentially of natural sources of algae, alpha carotene, beta carotene, gamma carotene, lutein, lycopene, xynthines, beta-cyptoxanthin, zeaxanthin, astaxanthin, phytoene, canthaxanthin, fucoxanthin and mixtures thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The specific example below will enable the invention to be better understood. However, they are given merely by way of guidance and do not imply any limitation.

The following is a discussion of etiologic risk factors, and epidemiologic, laboratory and intervention studies with antioxidants alone or in combination with statins and/or niacin. It identifies the possible reasons for inconsistent results. The discussion also proposes a scientific rationale for why nutritional formulations may improve the efficacy of standard therapy in the prevention or treatment of CAD.

I. Etiologic Risk Factors for CAD

Several investigations have identified risk factors for the development of CAD. These include a family history, age, High LDL-cholesterol and low HDL-cholesterol, high saturated fat intake, hypertension, physical inactivity, cigarette smoking, obesity, diabetes mellitus, inflammatory reactions and coronary calcium level. The combination of these risk factors may increase the risk or rate of progression of CAD more then that produced by any one individual risk factor. One of the mechanisms of most of these diverse risk factors, such as inflammatory reactions, cigarettes smoking and hyperglycemia, may involve the production of enhanced levels of free radicals. Free radicals derived from oxygen and nitrogen, referred to as reactive oxygen species (ROS) and reactive nitrogen species (RNS), can damage lipids, proteins, RNA and DNA. Although certain levels of free radicals are essential for driving the biologic reactions necessary for human survival, excess levels of these free radicals can increase the risk of most human chronic diseases, including CAD.

A. Oxidative Damage, C-reactive Proteins and Cholesterol

LDL-cholesterol is commonly referred to as a "bad cholesterol" because it is easily oxidizable by free radicals. Oxidized LDL-cholesterol may be on of the early events that could initiate plaque formation by increasing the formation of foam cells in the arterial wall; enhancing platelet adhesion and aggregation, triggering thrombosis and impairing elasticity of the coronary arteries. Oxidized LDL-cholesterol can also increase vascular smooth muscle cell proliferation by activating c-myc, and its binding partner MAX, and the carboxy-terminal domain-binding factors activator protein-2 (AP-2), and elongation 2 factor (E2F) in human coronary artery smooth muscle cells. The importance of c-myc in the progression of atherosclerosis lesions is demonstrated by the fact that gene therapy, by decoy/oligodeoxynucleotide which inactivates E2F, delivered to human bypass vein grafts intraoperatively, caused fewer graft occlusions and critical stenosis after 12 months.

Oxy LDL-cholesterol is also engulfed by macrophages to form foam cells, and C-reactive protein increases uptake of oxy LDL-cholesterol by macrophages. Both foam cells and increased proliferation of vascular smooth muscle cells contribute to the formation of plaque in the coronary arteries. Thus lowering the level of LDL-cholesterol and preventing the oxidation of this form of cholesterol should reduce the initiation, as well as the progression, of CAD.

B. Endothelial Cells, Free Radicals and Homocysteine

Endothelial cells of the vascular wall are damaged by the free radicals and the secretory products of inflammatory reactions (i.e. free radicals, cytokines and prostaglandin $E^2$), as well as by homocysteine. Endothelieal cell-derived nitric oxide (NO) is a potent vasodilator that is formed during the metabolism of arginine, and it is responsible for regulating vascular tone. It is now recognized that endothelial cell dysfunction may also be one of the early events in the development of CAD.

Damage to endothelial cells may impair the nitric oxide synthase (NOS) pathway, which in turn may impair endothelium-dependent coronary artery dilation. Thus, deficiency in the production of NO may interfere with the function of the vessel wall. The level of inducible NOS (iNOS) mRNA in vascular smooth muscle cells of a healthy arterial wall is low, but the levels of iNOS mRNA and protein in macrophages and in the majority of early lesions and in all advanced artherosclerotic lesions are high. This suggests that these sources may release an excessive amount of NO that could increase the progression of coronary artery dysfunction. Thus, the role of NO in maintaining normal vascular function depends upon maintaining proper levels of NO.

Both deficiency and excess production of NO can impair vasomotion and can enhance endothelial dysfunction and vascular wall defect. Damaged endothelial cells reduce the release of nitric oxide (NO) which impairs the vasodilation arteries. Therefore, protecting the endothelial cells against free radicals may be considered helpful in prevention or treatment strategy. Once the plaque is formed, it serves as a continuous stimulus for increased inflammatory reactions that in turn causes gradual progressive increase in plaque size.

C. Development of Aspirin Resistance

Aspirin is commonly recommended for the primary prevention and treatment of CAD, because it reduces inflammatory reactions and production of prostaglandin $E^2$ ($PGE^2$) by inhibiting cyclooxygenase activity. $PGE^2$ is one of the major factors responsible for platelet aggregation. About 5-12% of cardiac patients develop resistance to aspirin and about 24% of patients taking aspirin become semi-responders. The exact mechanisms of aspirin resistance remain to be eludicated. It is possible that aspirin doses commonly used fail to suppress cycloxygenase activity, requiring physicians to increase aspirin doses. It is also possible that aspirin becomes ineffective in reducing the activity of cycloxygenase and/or that $PGE^2$ is produced non-enzymatically. The latter would make patients totally resistant to aspirin. It has been reported that the risk of major cardiac events may increase by about 3-fold in aspirin resistant patients. Therefore, resolving the issue of aspirin resistance becomes a new challenge for researchers in cardiology.

II. Role of Antioxidants in the Prevention and Treatment of CAD

In humans, different types of inorganic and organic free radicals derived from oxygen and nitrogen are produced. Oxygen-derived free radicals include o (anion), OH (hydroxyl free radicals), O (oxy free radicals), RO (peroxy free radical) and R (organic free radical). Nitrogen-derived free radicals include NO (nitric oxide) and NOOH (peroxynitrite). Humans also produce certain antioxidants such as antioxidant enzymes, glutathione, coenzyme Q10, alpha lipoic acid and NADH (nicotinamide adenine dehydrogenase, reduced form). They also consume antioxidants through their diet such as vitamin A, vitamin C, vitamin E, beta-carotene and other carotenoids, phenolic compounds and the mineral selenium (which acts as a cofactor or glutathione peroxidase).

These antioxidants, at least in part, have different affinities with various types of free radicals. With these complexities of relationship between antioxidant and oxidant reactions, it is not rational to utilize one or two antioxidants for the prevention or the treatment of any diseases, including CAD. In addition, an individual antioxidant, when it become oxidized, acts as a free radical. Therefore, the use of a single antioxidant in, for example, heavy smokers (men or women), who have a high oxidative body environment, to reduce the risk of an chronic diseases make no scientific sense. Unfortunately, most human trials in CAD involve one or two dietary antioxidants without consideration or internal oxidative environment and this may one of the major reasons for the inconsistent results.

Another reason could be that all intervention trials published thus far do not give proper consideration to the form of dietary antioxidants (natural vs. synthetic vitamin E and β-carotene (β-carotene having functions other than being a precursor of vitamin A), did not include d-alpha tocopherol as well as d-α-tocopheryl succinate (α-tocopheryl succinate being the most effective form of vitamin E) and did not include endogenously made antioxidants such as co-enzyme Q10, glutathione elevating agents (n-acteylcysteine) and alpha-lipoic acid.

A. Laboratory Studies

Most laboratory studies support the hypothesis that supplementation with antioxidants may prevent and reduce the rate of progression or atherosclerosis. For example, Vitamin E supplementation has been known to reduce the development of early aortic atherosclerotic lesions in chickens and rabbits. Further, stenosis progression was decreased in male monkeys receiving vitamin E supplementation in comparison to those receiving an unsupplemented atherosclerotic-promoting diet. The above studies utilized vitamin E alone. A high oxidative internal environment may not exist in rodents; therefore, it is unlikely that adverse effects of a single antioxidant can be observed in the animal model. This may not be true in humans, especially in heavy smokers. In addition, unlike in humans, the lifestyle and diet are fairly constant in these animal models.

B. Proposed Mechanism of Action Antioxidants

Several mechanisms of action of antioxidants in reducing the risk of CAD have been proposed, although most studies have focused on the action of vitamin E alone. For example, vitamin E reduces oxidation of membrane and LDL cholesterol, reduces c-myc activated pathways responsible for smooth muscle cell proliferation, reduces aggregation of platelets in normal subjects, type I diabetes patients and heart transplant recipients on cyclosporine, and inhibits the protein kinase C pathway.

Vitamin C prevents lipid oxidation and oxy LDL-cholesterol mediated pathway. Vitamin C also potentiates nitric oxide activity in normalizing vascular function in patients with cardiac disease associated with hypercholesterolemia, hyperhomocysteinemia, hypertension and smoking.

The combination of vitamin C and E produces a synergistic inhibition on LDL-cholesterol oxidation.

Alpha-tocopheryl succinate inhibits the expression of c-myc in some mammalian cells, and α-tocopheryl reduces the proliferation of vascular smooth muscle cell proliferation in cultures by inhibiting protein kinase C activity that independent of antioxidant properties.

Co-enzyme Q10 acts as a cofactor in the Kreb's cycle in mitochondria to generate ATP.

Alpha-lipoic acid improves glucose utilization in peripheral tissue by stimulating glucose transport and uptake. Therefore, it can improve the function of damaged muscle or endothelial cells.

SH-compounds such as glutathione are one of the most important intracellular antioxidants responsible for protecting cells against free radical damage. Oxidative damage can reduce the level of SH-compounds within the cells. Therefore, glutathione-elevating agents such as N-acetylcysteine (NAC) and α-lipoic acid may be useful in restoring intracellular levels of glutathione in endothelial cells and cardiac muscles, thereby improving the function of these cells and protecting them from further oxidative damage.

Thus, mechanistic data exist that support the rationale for using a mixture of dietary and endogenously made antioxidants in the prevention, and as an adjunct to standard therapy, in the treatment of CAD.

C. Epidemiological Studies

Epidemiological studies are a useful way to establish an association between dietary nutrients including antioxidants and the risk of CAD. However, some inherent complexities of the varied diet and lifestyle, techniques of data collection that rely on memory or shot-term dietary records and the multi-factorial nature of CAD, make it difficult for them to yield consistent rules. Nevertheless, 6 out of 8 epidemiologic studies that have been performed with vitamin E alone show an inverse relationship between vitamin E intake and the risk of CAD.

In particular, in a WHO/MONICA study there was a high inverse association between age-specific mortality from ischemic heart disease and lipid-standardized vitamin E levels. In a Polish study, plasma levels of vitamin E were significantly lower n patients with stable and unstable angina compared to healthy control persons. In a UK study, an inverse association between plasma vitamin E levels and risk of angina was reported. In a Harvard study of 39,910 male health professionals, a 36% lower relative risk of CAD was demonstrated among those consuming 60 IU vitamin E per day in comparison to those consuming less than 7.5 IU vitamin E per day. Men who took at least 100 IU vitamin E per day for at least 2 years had a 37% lower risk of CAD than those who did not take vitamin E. Another Harvard study of 87,245 healthy nurses with a follow-up period of 8 years revealed that women in the top fifth of vitamin E intake had a 34% lower relative risk of a major risk of CAD in comparison to those in the lowest fifth. The relative risk of CAD was 48% lower in women taking vitamin E supplements of more than 100 mg per day for at least 2 years. Vitamin E obtained only from the diet provided no such protection. In another US study of 11,000 people of age 67 or over, with a follow up period of 6 years, it was found that vitamin E supplementation was associated with a 47% reduction in mortality from CAD. Further reduction was observed in people who were taking vitamin E supplements together with vitamin C.

In contrast to the 6 investigations discussed above, 2 studies failed to observe any association between serum selenium, vitamin A or vitamin E and the risk of death from CAD. Because of numerous confounding factors associated with diet and lifestyle, epidemiologic studies have produced inconsistent results. It is surprising that most studies have shown inverse relationship between vitamin E intake and the risk of CAD.

D. Intervention Studies in Humans

CAD is considered a multi-factorial disease that involves multiple risk factors such as increased oxidation and inflammatory reactions, high levels of LDL-cholesterol and low levels of HDL-cholesterol, as well as high levels of homocysteine and glucose. Each of these risk factors may contribute variable degrees of risk to the initiation and progression of CAD. Therefore, the purpose of any intervention trials should be to attenuate these risk factors for CAD. This would require a multifunctional approach involving, statin with or without niacin, multiple dietary and endogenously made antioxidants, B-vitamins and mineral selenium, and aspirin. Unfortunately, to date no such studies have been performed.

The clinical studies that have been published have produced inconsistent results. This is due to the fact that form, type, number, dose and dose-schedule of antioxidants, study end points, observation period and patient population differ from one study to another. When antioxidants were used in combination with cholesterol—lowering drugs, similar inconsistent results for the same reasons were also noted.

The published intervention trials can be divided into four groups, (a) those using a single dietary antioxidant in patients with no prior cardiac events; (b) those using a single dietary antioxidant in patients with prior cardiac events; (c) those using two or more dietary antioxidants with or without prior cardiac events; and (d) those using one or more dietary antioxidants in combination with cholesterol-lowering drugs in patients with or without prior cardiac events. Each of these is discussed below.

1.) Intervention Trials with One Dietary Antioxidant in Patients with No Prior Cardiac Event A summary of 5 intervention trials involving the use of one dietary antioxidant in patients with no prior cardiac events is presented in Table 1 below. Data showed that dose and type of antioxidants, population type, study endpoint and follow-up period differ from one study to another. Nevertheless, three studies showed the beneficial effects of dietary antioxidants, one study reported no beneficial effect and another investigation showed an adverse effect.

For example, vitamin E supplementation (544 IU) improved endothelial-dependent flow-mediated dilation (FMD) of blood vessels in smokers with hypercholesterolemia. An elevation of plasma homocysteine by methionine impaired endothelial function in healthy make subjects. Pre-treatments with vitamin C (2 g/day) prevent this effect and reduced arterial stiffness. In the Cambridge Heart Antioxidant Study (CHAOS) involving 2002 patients with angiographically proven coronary atherosclerosis, it was found that patients receiving 400 or 800 IU of vitamin E per day for a median follow-up period of 510 days (about 18 months) had a 77% lower risk of non-fatal myocardial infarction that the placebo group. However, a small (18%) but statistically significant increase in cardiovascular death was observed in the vitamin E group. The investigators suggested that most of the deaths in the vitamin E group occurred in the early part of the follow-up period; and therefore, they were unlikely due to vitamin E.

In contrast to the above observation, vitamin E supplementation in the HOPE trial involving 9,541 patients with high risk for cardiac events (atherosclerotic disease, diabetes plus one cardiac risk factor such as hypertension, elevated total cholesterol, low HDL cholesterol, cigarette smoking or documented microalbumineria), but without any evidence of heart failure, did not reduce death, stroke or non-fatal myocardial infarction in comparison to control. The exact reasons for this discrepancy between CHAOS and HOPE trials are unknown. However, it was pointed out that the HOPE trial used vitamin E (400 IU) from natural sources that had α-tocopherol and tocotrienol, and that the α-tocopherol portiaon was only about 50 IU. It was suggested that larger doses of aαtocopherol may be required to reduce the inflammation and atherogenesis.

Another study showed that daily consumption of 800 IU of vitamin E increased the levels of oxidative stress markers in heavy smokers. This was expected because vitamin E in the presence of an elevated level of oxidative environment oxidized that is present in heavy smokers was oxidized and acted as a free radical. Among non-smokers, vitamin E may produce transient benefits on certain criteria, but it would be ineffective on a long-term basis. Therefore, both CHAOS and HOPE trials have serious limitations, since they have utilized only vitamin E. From the studies presented in this section, no conclusion regarding the value of antioxidants for the prevention or treatment of CAD can be drawn.

TABLE 1

Summary of intervention trials with vitamin E or vitamin C in high risk patients with no prior cardiac events

| Name of Study | No. of Patients | Type of Antioxidant | Criteria of Study | Follow-up Period | Results |
|---|---|---|---|---|---|
| HOPE | 9,541[a] | Vitamin E 400 IU | Death, stroke Non-fatal MI | 4.5 y | no effect |
| CHAOS | 2,002[b] | Vitamin E (d-αT) 400 or 800 IU | Death, non-fatal MI | 510 d | reduced |
| — | 42[c] | Vitamin E(α-TA) 544 IU | FMD | 4 months | improved |
| — | 10[d] | Vitamin E 800 IU | Oxidative stress | 3 weeks | increases |
| — | 80[e] | Vit. C-2 g Methione-100 mg/kg | Plasma homocysteine, arterial stiffness | 6 hours | reduced |

HOPE (Heart Outcomes Prevention Evaluation);
CHAOS (Cambridge Heart Antioxidant Study);
MI (myocardial infarction);
FMD (endothelial-dependent flow-mediated dilation)
[a]High risk for cardiac events (known atherosclerotic disease, diabetes plus one cardiac risk factor such as hypertension, elevated total cholesterol, low HDL cholesterol, cigarette smoking or documented microalbumineria), and not have heart failure.
[b]Proven atherosclerotic disease
[c]Hypercholesterolemia, smoke and smokers with hypercholesterolemia
[d]Heavy smokers
[e]Healthy male subjects receiving methionine to increase homocysteine levels 2.) Intervention Trials Utilizing Only Vitamin E in Patient with Prior Cardiac Events A summary of 4 intervention trials using only vitamin E in high-risk patients with prior cardiac events is presented in Table 2 below. Results showed that doses of vitamin E, patient population, study endpoint and follow-up periods differ from one investigation to another. Nevertheless, three of four studies showed beneficial effects of vitamin E and one study revealed that the use of a low dose f vitamin E was ineffective.

For example, in a trial involving 100 patients having coronary angioplasty, those receiving 1200 IU of vitamin E daily for a 4-month period showed restenosis in 34.6% of patients, whereas those receiving a placebo showed stenosis in 50% of patients. In another study involving 75 patients, those receiving α-tocopherol (1200 IU/day) for a period of 5 months has lowered C-reactive proteins and monocyte interleukin-6 in diabetes type 2 patients with or without macrovascular complications in comparison to BMI-matched healthy controls. In still another study, supplementation with α-tocopherol (800 IU) decreased LDL-C oxidation in patients with chronic renal failure, but the benefit was greater in patients with peritoneal dialysis than that in hemodialysis.

In contrast to the above three studies, results of the ATBC trial involving 1862 men for a period of 6 years showed no significant difference in the number of major coronary events or cardiovascular death between the vitamin E group (50 mg/day) and placebo group. This study has utilized a much lower dose of vitamin E than the previous four studies. This could explain the above inconsistency in results. Again using only one dietary antioxidant in these trials may not be significant for cardiac prevention or treatment.

TABLE 2

Summary of intervention trials with vitamin E alone in high risk patients with prior cardiac events

| Name of Study | No. of Patients | Type of Antioxidant | Criteria of Study | Follow-up Period | Results |
|---|---|---|---|---|---|
| — | 100[a] | Vitamin E 1200 IU | Stenosis | 4 months | reduced |
| — | 75[b] | Vitamin E 1200 IU | C-reactive protein | 5 months | reduced |
| — | 33[c] | Vit. E (d-αT) 800 IU | LDL oxidation | 12 weeks | reduced |
| ATBC | 1862[d] | Vitamin E 50 mg | Death, CAD events | 6 y | no effect |

3.) Intervention Trials Utilizing Two or More Antioxidants in Patients with or without Prior Cardiac Events A summary of 9 interventional trials with two or more antioxidants in high risk patients with or without prior cardiac events is presented in table 3 below. Results showed that dose, type and number of antioxidants, patient population, study endpoint and follow-up periods differ from one study to another. Nevertheless, six studies showed beneficial effects, one study revealed no beneficial effect while two revealed harmful effects.

In a double blind randomized prospective study, supplementation with 500 mg vitamin C and 400 IU vitamin E twice daily retarded progression of transplant associated cardiac arthrosclerosis. Supplementation with vitamin E and slow release vitamin C also reduced atherosclerosis. Another study has reported that supplementation with tomato juice (500 ml/day). Vitamin C (500 mg/day) and vitamin E (800 IU/day) decreased oxidation of LDL cholesterol and plasma levels of C-reactive proteins in type 2 diabetes patients. It has been suggested that vitamin C may slow atherogenesis by improving endothelial-dependent vasodilation in patient with hyperglycemia and abnormal lipids, perhaps by preventing oxidation by nitric oxide. Pretreatment with 800 IU of vitamin E and 1000 mg of vitamin C prevented the above action of a high fat diet on endothelium-dependent vasodilation of the brachial artery. A clinical trial involving 317 patients who received a placebo or multiple antioxidants (700 IU vitamin E, 500 mg vitamin C and 30,000 IU beta-carotene) or probucol 4 weeks before and 6 months after undergoing angioplasty procedures, showed no significant difference in the rates of restenosis between the vitamin group and placebo group; however, probucol, a powerful antioxidant, was effective in reducing the restenosis. Another study has shown that supplementation with multiple vitamins reduced the homocysteine level and LDL-cholesterol oxidation. Among CARET participants, supplementation with 30 mg β-carotene and 25,000 IU retinyl palmitate for a 5-year period did not change lipid levels. This may be due to the fact that only vitamin A and its precursor were used in this study and this may not be sufficient to alter lipid levels. In the ATBC trial involving 1862 heavy smokers, supplementation with 50 mg vitamin E and 20 mg β-carotene for a period of 5.3 years increased major cardiac risks. This may be due to the fact that doses of these antioxidants were low and male heavy smokers had high levels of oxidative environment. This could have resulted in rapid oxidation of these antioxidants, thereby increasing the CAD risk factors. Supplementation with vitamin C (500 mg/day) and vitamin E (800 IU/day) increased the risk of atherosclerosis among post-menopausal women with a history of varying levels of stenosis. Again, no conclusion regarding the value of antioxidants in prevention or treatment of CAD can be made, because endogenously made antioxidants varied from one study to another.

TABLE 3

Summary of intervention trials with two or more antioxidants in high risk patients with or without prior cardiac events

| Name of Study | No. of Patients | Type of Antioxidant | Criteria of Study | Follow-up Period | Results |
|---|---|---|---|---|---|
| — | 19[c] | Vit. E-400 IU Vit. C-500 mg | Coronary Atherosclerosis | 1 y | reduced |
| — | 520[f] | Vit. E, slow release vit. C | Atherosclerosis | 6 y | reduced |
| — | | tomato juice 15 ml/d, vit C 500 mg, vit E 800 IU | OxyLDL-C, C-reactive protein | | decreased |
| — | 20[e] | Vitamin E 800 IU Vitamin C-1 g | FMD | 6 h | increased |
| — | 317[d] | Probucol-500 mg Vitamin E-700 IU Vitamin C-500 mg β-carotene-30,000 I | Restenosis | 5-7 mo | probucol reduced more than combination |
| | 182[f] | Multivitamins | homocysteine, LDL-C oxidation | 6 mo | Reduced |
| CARET | 52[a] | β-Carotene-30 mg Retinyl palmitate-25000 IU | Lipid levels | 5 y | no effect |

TABLE 3-continued

Summary of intervention trials with two or more antioxidants in high risk patients with or without prior cardiac events

| Name of Study | No. of Patients | Type of Antioxidant | Criteria of Study | Follow-up Period | Results |
|---|---|---|---|---|---|
| ATBC | 1862[b] | Vit E (α-T)-50 mg β-carotene-20 mg | Major cardiac | 5.3 y | increased |
| Wave | 423[g] | Vit E 800 IU; vitamin C 1 g | Stenosis | 2.8 y | increased |

CARET (Carotene Retinol Efficacy Trial);
ATBC (Alpha-Tocopherol Beta-Carotene Cancer Prevention Study);
WAVE (Women's Angiographic Vitamin and Estrogen);
FMD (endothelial-dependent flow-mediated dilation). All vitamins were given once a day until specified otherwise.
[a] and [b] = male heavy smokers;
[c] = cardiac transplant;
[d] = angioplasty;
[e] = normal individuals consuming high-fat meal;
[f] = hypercholesterolemic;
[g] = post-menopasual women with 15-75% stenosis;
[h] = type II diabetes patients.

4.) Intervention Trials Utilizing One or More Antioxidants in Combination with Cholesterol-lowering Drugs Inpatients with or without Prior Cardiac Events.

A summary of 6 interventional trials with one or more antioxidants in combination with cholesterol-lowering drugs in high risk patients with or without prior cardiac events is described in Table 4 below. The number, type, dose and dose schedules of antioxidants, patient population, observation period and criteria of study were different. Three studies revealed beneficial effects, one showed no beneficial effects, whereas two investigations by the same group showed deleterious effects when combined with simnastatin-niacin.

It has been reported that vitamin E supplementation (300 IU/day) together with simvastatin for an 8 week period improved endothelial-dependent flow-mediated dilation (FMD) as well as endothelial-dependent nitroglycerine-mediated dilation (NMD) in the brachial artery of patients with hypercholesterolemia more that they produced simvastatin alone. A short-term beneficial effect may be obtained by high doses of a single antioxidant. Indeed, it has been reported that coenzyme Q10 has been shown to be useful in improving the function of damaged cardiac muscle associated with congestive heart failure and idiopathic dilated cardiomyopathy. In these instances, coenzyme Q10 probably improves the mitochondrial function of damaged cardiac muscles and protects them from further injury.

One study using 156 men with previous coronary bypass surgery who were receiving a cholesterol-lowering drug combination (colestipol-niacin) alone or in combination with vitamin E 100 IU per day showed that the vitamin E treated group revealed less progression of the narrowing of their coronary arteries in comparison to cholesterol lowering drugs alone during a 4-year trial period In the Heart Protection Study involving 20,500 patients with high risk, supplementation with antioxidants vitamins (vitamins E 650 mg, vitamin C 250 mg and β-carotene 20 mg) together with simvastatin for a period of 5.5 years did not interfere with the beneficial statin. Doses of antioxidants were small in this study, and endogenously made antioxidants were not included in the antioxidant regimen. Opposite results were obtained by recent clinical studies in which vitamin C, 1000 mg, vitamin E as d-α-tocopherol, 800 IU, natural beta-carotene, 25 mg and selenium, 100 mg per day were given together with mevastatin-niacin in a subset of patients with low level of HDL-cholesterol. Results revealed that niacin-induced elevation of HDL cholesterol was blocked by antioxidant supplements. This has not been reproduced by another clinical study; and therefore, the value of this investigation remains uncertain. In addition, dietary antioxidants vitamin A and β-carotene, and endogenously made antioxidants, n-acetylcysteine (a glutathione-elevating agent), α-lipoic acid, and co-enzyme Q10 as well as B-vitamins were missing from their formulation.

The same group of investigators, using the same formulation, reported that a mixture of dietary antioxidants reduced the degree of proximal artery stenosis in comparison to placebo controls. However, in combination with simvastatin it was less effective than the simvastatin-niacin group. Because of the small sample size (40 patients per group) and unusually large variation in the results (200-700% variation around the mean value), no conclusion regarding the value of antioxidant in the prevention or treatment of CAD can be drawn. The same group using the same mixture of dietary antioxidants reported that treatment of patients with simvastin plus niacin alone or with the dietary antioxidants significantly reduced total cholesterol, LDL-cholesterol and triglycerides, and increase HDL-cholesterol levels in comparison to those who were not treated. There was no significant difference between those receiving simvastatin plus niacin or those receiving simvastatin, niacin and antioxidants.

Analysis of plasma levels of noncholesterol sterols suggested that lathosterol was directly and β-sitosterol was inversely related to stenosis. It was interesting to note that treatment with simvastatin plus niacin or simvastatin, niacin and antioxidants, decreases the level of lathosterol and increases the level of β-sitosterol to similar degrees. These data suggest that newly identified predictors of stenosis were not significantly affected by the addition of antioxidants to the group receiving simvastatin plus niacin. Nevertheless, the investigators concluded that antioxidants prevent the efficacy of simavastatin plus niacin treatment.

Most intervention studies have recommended taking supplements once a day. Based on the biological-half like of antioxidants that varies from 6-10 h, the recommendation of taking antioxidants once a day may not produce an optimal effect on the prevention or as an adjunct to standard therapy in the treatment CAD. The two clinical studies have attracted the attention of cardiologists and primary care physicians, and have led them to believe that antioxidants have either no value or may adversely affect the strategy for cardiac prevention and treatment. However, the analysis of their data suggests that such conclusion may be premature. Based on conflicting results of intervention trials with one or more dietary antioxidants and lack of data on appropriately designed clinical trials with multiple dietary and endogenously made antioxidants, it is not appropriate to propagate an idea that antioxidants may harm patients with cardiac risks, and that they have no role in prevention or treatment of CAD.

protein in mammalian cells in culture, whereas vitamin A treatment does not produce such an effect. Vitamin A can induce cell differentiation in certain normal and cancer cells, whereas BC does not. The gradient of oxygen pressure varies within the cells. Vitamin E is more effective as a quencher of free radicals in reduced oxygen pressure, whereas BC and vitamin A are more effective in higher atmospheric pressure. Vitamin C is necessary to protect cellular components in

TABLE 4

Summary of intervention trials with one or more antioxidants in combination with cholesterol-lowering drugs in high risk patients with or without prior cardiac events

| Name of Study | No. of Patients | Type of Antioxidant + Cholesterol-lowering drugs | Criteria of Study | Follow-up period | Results |
|---|---|---|---|---|---|
| — | 7[a] | Simvastatin + vit.E-300 IU | FMD NMD | 8 weeks | improved |
| — | 126[b] | Standard therapy + Co-enzyme Q10 33.3 mg (thrice/day) | Cardiac muscle function | 6 y | improved |
| CLAS | 156[c] | Colestipol + niacin Vit. E-100 IU or more | Progressive Atherosclerosis | 2 y | reduced |
| HPS | 20,500[d] | Simvastatin + Vit.E-650 mg Vit. C-250 mg- carotene-20 mg | Cardiac events | 5.5 y | no better than than drug alone |
| HATS | 160[e] | Simvastatin + niacin + Vit.E-800 IU, Vit.C-1 g- carotene-25 mg, selenium-100 mcg (N = 46) | Stenosis | 3 y | reduced drug effectiveness but was more effective than control |
| HATS | 153[e] | Same | HDL | 1 y | reduce drug effectiveness |

CLAS (Cholesterol-Lowring Antherosclerosis Study);
HPS (Heart Protection Study);
HATS (HDL-atherosclerosis Treatment Study);
FMD (endothelium-dependent flow-mediated dilation);
NMD (endothelium-independent nitroglycerine-mediated dilation);
HDL—(high density lipoprotein cholesterol);
N (sample size for group). All vitamins were given once a day until specified otherwise;
[a] = hypercholerstolemia;
[b] = idiopathic dilated cardiomyopathy;
[c] = coronary bypass surgery;
[d] = women, elderly diabetes, people with low baseline cholesterol pre-treatment and those prior occlusive non-coronary vascular disease;
[e] = coronary disease with low HDL-cholesterol.

III. Scientific Rationale for Using Multiple Dietary and Endogenously Made Antioxidants, and B-vitamins and Minerals in the Prevention or as Adjunct to Standard Therapy in the Treatment of CAD.

Since increased production of free radicals may be involved in the initiation and progression of CAD, the use of antioxidants appears to be a rational choice for the prevention and treatment of this disease. The use of single antioxidants for the prevention or treatment of CAD is not recommended because antioxidants act as free radicals when oxidized. Instead, the present invention, as described below, involves use of formulations incorporating multiple dietary and endogenously made antioxidants because many different types of free radicals are produced and each antioxidant has a different mechanism of action and has a different affinity for each of these free radicals, depending upon the cellular environment.

For example, β-carotene (BC) is more effective in quenching oxygen radicals than most other antioxidants. BC can perform certain biological functions that cannot be carried out by its metabolite, vitamin A and vice versa. In particular, it has been reported that BC treatment enhances the expression of the connexin gene, which codes for a gap junction aqueous environments, whereas carotenoids, vitamins A and E protect cellular components in non-aqueous environments. Vitamin C also plays an important role in maintaining cellular levels of vitamin E by recycling the vitamin E radical (oxidized) to the reduced (antioxidant) form.

Also, the oxidative DNA damage produced by oxidized vitamin C could be ameliorated by vitamin E. The form and type of vitamin E used are also important in any clinical trial. It is known that various organs of rats selectively absorb the natural form of vitamin E. It has been established that α-tocopherol-succinate (α-TS) is the most effective form of the vitamin. The inventors have reported that oral ingestion of α-TS (800 IU/day) in humans increased plasma levels of not only α-tocopherol, but also α-TS, suggesting that α-TS can be absorbed from the intestinal tract before hydrolysis to α-tocopherol. Selenium is a co-factor of glutathione peridodase, and Se-glutathione peroxidase also acts as an antioxidant. Therefore, selenium supplementation together with other antioxidants is also essential.

Glutathione, an endogenously produced compound, represents a potent intracellular protective agent against damage produced by free radicals. It catabolizes H202 and anions. However, oxidized glutathione may make the cell more sensitive to further oxidative injuries. Therefore, increasing the intracellular levels og glutathione in vascular endothelial cells, vascular smooth cells and cardiac muscles, may be very useful in the management of CAD. Oral supplementation with glutathione failed to significantly increase plasma levels of glutathione in human subjects, suggesting that this tripeptide is completely hydrolyzed in the G.I. tract. N-acetylcysteine and α-lipoic acid increase the intracellular levels of glutathione, and therefore, they can be used in combination with dietary antioxidants.

Furthermore, damaged vascular endothelial cells and cardiac muscle cells may not produce sufficient amounts of ATP due to a reduction in the synthesis of coenzyme Q10. Therefore, supplementation with coenzyme Q10 may be necessary for prevention, and as an adjunct to standard therapy for the treatment of CAD. In addition t being a weak antioxidant, coenzymeQ10 acts as a co-factor for generating ATP in mitochondria. It also scavenges peroxy radicals faster than α-tocopherol, and like vitamin C, can regenerate E in a redox cycle. B-6, B-12 and folic acid are essential for reducing the level of homocysteine.

IV. Antioxidants and Aspirin Resistance

It has been reported that antioxidants in combination with aspirin is more effective in inhibiting cyclooxygenase activity than either agent administered by itself. Alph tocopherol succinate has been shown to reduce the action of $PGE^2$ on adenylate cyclase. Thus, antioxidants can prolong the efficacy of aspirin among semi-responders and may prevent platelet aggregation among those who have developed total resistance.

The following discusses the scientific rationale behind the inventors' inclusion of multiple dietary and endogenously made, antioxidants, and B-vitamins and minerals in the formulations of the invention, which formulations have been determined by the inventors to be useful in preventing CAD, and/or as an adjunct to standard therapy in the treatment of CAD:

Statin with or without niacin, and aspirin are considered standard therapy for the prevention and treatment of CAD. The invention described and claimed herein comprises nutritional formulations specific to medium risk patients (patients taking medication but had no cardiac events) and high risk patients (patients taking medications with one or more cardiac events). The formulations of the invention contain multiple dietary and endogenously made antioxidants, B-vitamins including B-6. B-12 and folic acid and minerals including selenium (selenomethionine) that would enhance the efficacy of standard therapy for the prevention and treatment of CAD.

In one embodiment, the invention provides a formulation and a method for at least one of substantially preventing and treating coronary artery disease in an individual I need of the same, which method comprises administering to such individual a therapeautically effective amount of a formulation comprising the following components in about the following ranges. As used herein, the term "about" shall be construed to mean±10%.

|  | Total Dose/day |
|---|---|
| Vitamin A (palmitate) | 3,000-5,000 I.U. |
| Beta-carotene (from natural D. salina) | 10-20 mg |
| Vitamin D-3 (cholecalciferol) | 400-600 I.U. |

-continued

|  | Total Dose/day |
|---|---|
| Natural source Vitamin E |  |
| (d-alpha tocopherol) | 50-400 mg |
| (d-alpha tocopheryl acid succinate) | 100 I.U. |
| Buffered Vitamin C (calcium ascorbate) | 100-4,000 mg |
| Thiamine mononitrate | 2-10 mg |
| Riboflavin | 2-20 mg |
| Niacinamide ascorbate | 15-200 mg |
| d-calcium pantothenate | 5-30 mg |
| Pyridoxine hydrochloride | 2-10 mg |
| Cyanocobalamin | 5-20 mcg |
| Folic Acid (Folacin) | 400-1,200 mcg |
| D-Biotin | 100-500 mcg |
| Selenium (l-seleno-methionine) | 50-200 mcg |
| Chromium picolinate | 50-200 mcg |
| Zinc Glycinate | 10-30 mg |
| Calcium citrate | 100-500 mg |
| Magnesium citrate | 100-250 mg |
| Vitamin C | 100-4,000 mg |
| d-α-tocopheryl succinate | 50-400 I.U. |
| N-acetylcysteine | 100-500 mg |
| Alpha-lipoic acid | 15-100 mg |
| Coenzyme Q10 | 10-250 mg |
| Omega-3 fatty acid | 1,000-2,000 mg |

Example embodiments of recommended ingredients and doses of the proposed nutritional formulations are presented below in Table 5. Because of the variation in the biological half-life of antioxidants (6-10 h), it is recommended (nut not required) to ingest the formulation twice per day, i.e. half in the morning and half in the evening, before a meal. The proposed doses are safe.

TABLE 5

Recommended doses of dietary and endogenously made antioxidants, B-vitamins and selenium for the prevention and treatment of CAD

| Risk level | Recommendation per day |
|---|---|
| Medium risk | SEVAK ®[1], a multiple dietary antioxidant with B-Vitamins and selenomethionine, but, with no Fe, Cu or Mn. In addition to SEVAK ®[1], the formulation contains vitamin C, about 1000 mg; d-α-tocopheryl succinate, about 200 IU; N-acetylcysteine, about 250 mg; alpha-lipoic acid, about 30 mg; coenzyme Q10, about 30 mg; and omega-3 fatty acid, about 1000 mg. |
| High risk | SEVAK ®[1], a multiple dietary antioxidant with B-Vitamins, selenomethionine, but no Fe, Cu or Mn. In addition to SEVAK ®[1], the formulation contains vitamin C, about 2000 mg; d-α-tocopheryl succinate, about 600 IU; N-acetylcysteine, about 500 mg; alpha-lipoic acid, about 60 mg; coenzyme Q10, about 90 mg; and omega-3 fatty acid, about 2000 mg. |

Medium risk: Patients taking medications without any cardiac events;
High risk: patients taking medications with one or more cardiac events.
[1]The formulation of SEVAK ®, which is commercially available from Premier Micronutrient Corporation, the owner of the present application, comprises the following components in about the following amounts:

|  | Total Dose/Day |
|---|---|
| Vitamin A (palmitate) | about 5,000 I.U. |
| Beta-carotene (from natural D. salina) | about 15 mg |
| Vitamin D-3 (cholecalciferol) | about 400 I.U. |
| Natural source Vitamin E |  |
| (d-alpha tocopherol) | about 100 I.U. |
| (d-alpha tocopheryl acid succinate) | about 100 I.U. |
| Buffered Vitamin C (calcium ascorbate) | about 500 mg |
| Thiamine mononitrate | about 4 mg |
| Riboflavin | about 5 mg |
| Niacinamide ascorbate | about 30 mg |
| d-calcium pantothenate | about 10 mg |

TABLE 5-continued

Recommended doses of dietary and endogenously made antioxidants, B-vitamins and selenium for the prevention and treatment of CAD

| Risk level | Recommendation per day |
|---|---|
| Pyridoxine hydrochloride | about 5 mg |
| Cyanocobalamin | about 10 mcg |
| Folic Acid (Folacin) | about 800 mcg |
| D-Biotin | about 200 mcg |
| Selenium (l-seleno-methionine) | about 100 mcg |
| Chromium picolinate | about 50 mcg |
| Zinc Glycinate | about 15 mg |
| Calcium citrate | about 250 mg |
| Magnesium citrate | about 125 mg |

In one embodiment, the present invention additionally recommends a diet low in fat, and high in fiber and antioxidants, regular exercise, reduced stress and coffee consumption, and no tobacco smoking.

Doses of antioxidants higher than those proposed in these formulations have been used to treat human diseases without any toxic effects. Nevertheless, it is important to describe briefly the known doses of antioxidants that could produce some toxicity. Daily consumption of vitamin A at doses higher than twice the Recommended Daily allowance (RDA) could produce liver and skin toxicity after prolonged consumption in adults. Vitamin C at doses of 10 g/d or more, when consumed in a single dose in the form of ascorbic acid, can cause upset stomach and diarrhea in some cases. Persons with kidney disease and hemochromotosis may have adverse effects to high doses of vitamin C. Vitamin E doses up to 2,000 IU/d have been used for short-term clinical studies without adverse effects; however, intravenous administration of 2,000 IU/day can cause clotting disorders which are reversible by vitamin K. Beta-carotene doses of 100 mg/d or more can cause yellowing of skin and pigment deposits in the eye are reversible upon discontinuation. N-acetylcysteine at doses of 1000 mg/day or more can cause trace metal deficiencies. Coenzyme Q10 doses up to 300 mg/d or more have no known toxicity in humans.

In another embodiment, the formulation consists essentially of:
Vitamin A (Palmitate) from about 3,000 to about 5,000 I.U.,
Vitamin E from about 50 to about 400 I.U.
Vitamin C from about 100 to about 4,000 I.U.,
Vitamin D$_3$ (Cholecalciferol) from about to about 400 to about 600 I.U.,
B Vitamins from about 2 to about 1,200 mg,
Biotin from about 100 to about 500 mcg,
Pantothenic Acid (as D-Calcium Pantothenate) from about 5 to about 30 mg,
Calcium Citrate from about 100 to about 500 mg,
Magnesium Citrate from about 100 to about 250 mg,
Zinc Glycinate from about 10 to about 30 mg,
Selenium (Seleno-L-Methionine) from about 50 to about 200 mcg,
Chromium (as Chromium Picolinate) to about 50 to about 200 mcg,
N-Acetyl Cysteine (NAC) from about 100 to about 500 mg,
Coenzyme Q$_{10}$ from about 10 to about 250 mg,
Alpha Lipoic Acid from about 15 to about 100 mg,
Omega-3 Fatty Acid from about 1,000 to about 4,000 mg,
L-Carnitine from about 50 to about 500 mg, and
Natural Mixed Carotenoids from about 10 to about 20 mg.

In another further embodiment, the present invention relates to a hearing health formulation comprising first and second compositions, and the first composition consisting essentially of:
Vitamin A (Palmitate) from about 3,000 to about 5000 IU
Vitamin E from about 50 to about 400 IU
Buffered Vitamin C (Calcium Ascorbate) from about 100 to about 4,000 mg
Vitamin C from about 100 to about 4,000 mg
Vitamin D$_3$ (Cholecalciferol) from about 400 to about 600 IU
Vitamin B$_1$ (Thiamine Mononitrate) from about to 2 about 10 mg
Vitamin B$_2$ (Riboflavin) from about 2 to about 20 mg
Vitamin B$_3$ (Niacinamide Ascorbate) from about 15 to about 200 mg
Vitamin B$_6$ (Pyridoxine Hydrochloride) from about 2 to about 10 mg
Folic Acid from about 400 to about 1500 mcg
Vitamin B$_{12}$ (Cyanocobalamln) from about 5 to about 20 mcg
Biotin from about 100 to about 500 mcg
Pantothenic Acid (as D-Calcium Pantothenate) from about 5 to about 30 mg
Calcium Citrate from about 100 to about 500 mg
Magnesium Citrate from about 100 to about 250 mg
Zinc Glycinate from about 10 to about 30 mg
Selenium (Seleno-L-Methionine) from about 50 to about 200 mcg
Chromium (as Chromium Picolinate) from about 50 to about 200 mcg, said the second composition consisting essentially of:
N-Acetyl Cysteine (NAC) from about 100 to about 500 mg
Coenzyme Q$_{10}$ from about 10 to about 250 mg
Alpha Lipoic Acid from about 15 to about 100 mg
Omega-3 Fatty Acid from about 1,000 to about 4,000 mg
Natural Mixed Carotenoids from about 10 to about 20 mg and
L-Carnitine from about 50 to about 500 mg Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A micronutrient formulation consisting of first and second compositions, said first composition consisting of:
Vitamin A (Palmitate) from about 3,000 to about 5000 IU
Vitamin E from about 50 to about 400 IU
Buffered Vitamin C (Calcium Ascorbate) from about 100 to about 4,000 mg
Vitamin C from about 100 to about 4,000 mg
Vitamin D$_3$ (Cholecalciferol) from about 400 to about 600 IU
Vitamin B$_1$ (Thiamine Mononitrate) from about to 2 about 10 mg
Vitamin B$_2$ (Riboflavin) from about 2 to about 20 mg
Vitamin B$_3$ (Niacinamide Ascorbate) from about 15 to about 200 mg
Vitamin B$_6$ (Pyridoxine Hydrochloride) from about 2 to about 10 mg
Folic Acid from about 400 to about 1500 mcg
Vitamin B$_{12}$ (Cyanocobalamln) from about 5 to about 20 mcg
Biotin from about 100 to about 500 mcg
Pantothenic Acid (as D-Calcium Pantothenate) from about 5 to about 30 mg
Calcium Citrate from about 100 to about 500 mg
Magnesium Citrate from about 100 to about 250 mg Zinc Glycinate from about 10 to about 30 mg
Selenium (Seleno-L-Methionine) from about 50 to about 200 mcg
Chromium (as Chromium Picolinate) from about 50 to about 200 mcg,
said second composition consisting of:
N-Acetyl Cysteine (NAC) from about 100 to about 500 mg
Coenzyme $Q_{10}$ from about 10 to about 250 mg
Alpha Lipoic Acid from about 15 to about 100 mg
Omega-3 Fatty Acid from about 1,000 to about 4,000 mg
L-Carnitine from about 50 to about 500 mg and
Natural Mixed Carotenoids from about 10 to about 20 mg and
wherein said formulation is designed to treat heart and pulmonary diseases and disorders.

2. The formulation of claim 1 wherein Vitamin E is selected from a group consisting of d-alpha Tocopheryl Succinate from about 50 to about 400 IU, d-alpha Tocopheryl Acetate from about 50 to about 400 IU and mixtures thereof, and wherein said mixed carotenoids are selected from a group consisting of natural sources of algae, alpha carotene, beta carotene, gamma carotene, lutein, lycopene, xynthines, beta-cryptoxanthin, zeaxanthin, astaxanthin, phytoene, canthaxanthin, fucoxanthin and mixtures thereof.

3. The formulation of claim 1 wherein said formulation is consumed by the user at least twice per day.

4. The formulation of claim 1 wherein said formulation is consumed by the user prior to diagnosis of pulmonary and heart related diseases.

5. The formulation of claim 1 wherein said formulation is consumed by the user for long term maintenance after diagnosis of pulmonary and heart diseases.

6. The formulation of claim 5 wherein long term maintenance is from about at least one week to about life long.

* * * * *